United States Patent
Teo et al.

(10) Patent No.: US 12,292,405 B2
(45) Date of Patent: May 6, 2025

(54) ELECTROCHEMICAL SENSOR FOR ANALYSIS OF BEVERAGES

(71) Applicant: Universal Biosensors Pty Ltd, Rowville (AU)

(72) Inventors: Stanley Zhen-Jin Teo, Victoria (AU); Peter Michael Newman, Victoria (AU); Ronald Christopher Chatelier, Rowville (AU); Luke Robert Cossins, Victoria (AU); Alastair M. Hodges, Victoria (AU)

(73) Assignee: Universal Biosensors Pty Ltd

( * ) Notice: Subject to any disclaimer, the term of this patent is extended or adjusted under 35 U.S.C. 154(b) by 502 days.

(21) Appl. No.: 17/765,434

(22) PCT Filed: Sep. 30, 2020

(86) PCT No.: PCT/IB2020/000827
§ 371 (c)(1),
(2) Date: Mar. 30, 2022

(87) PCT Pub. No.: WO2021/064466
PCT Pub. Date: Apr. 8, 2021

(65) Prior Publication Data
US 2022/0365023 A1    Nov. 17, 2022

Related U.S. Application Data

(60) Provisional application No. 62/908,561, filed on Sep. 30, 2019.

(51) Int. Cl.
*G01N 27/413*    (2006.01)
*G01N 27/30*    (2006.01)
(Continued)

(52) U.S. Cl.
CPC ......... *G01N 27/413* (2013.01); *G01N 27/302* (2013.01); *G01N 27/3277* (2013.01);
(Continued)

(58) Field of Classification Search
CPC .............. G01N 27/413; G01N 27/302; G01N 27/3277; G01N 27/3272; G01N 33/0047; G01N 33/14–146
See application file for complete search history.

(56) References Cited

U.S. PATENT DOCUMENTS 5,192,415 A    3/1993  Yoshioka et al.
5,651,869 A *  7/1997  Yoshioka ............... C12Q 1/006
                                                    435/14
(Continued)

FOREIGN PATENT DOCUMENTS

AU    2020276340 A1    12/2021
CN       109085218 A    12/2018
(Continued)

OTHER PUBLICATIONS

EPO machine-generated translation of CN 109085218 A, patent published Dec. 25, 2018 (Year: 2018).*
International Search Report, Feb. 11, 2021.

*Primary Examiner* — Alexander S Noguerola
(74) *Attorney, Agent, or Firm* — Aura IP Law, PC (57) ABSTRACT

The invention disclosed herein relates to a dry sensor for measuring the concentration of an analyte in a liquid beverage sample. Described herein is a novel dry sensor which is able to receive a liquid sample and adjust the pH of the liquid to be suitable for assaying an analyte of interest without the need to add reagents to the sample and/or to perform manually timed operations and able to detect a redox reaction in the presence of a liquid sample. The meter disclosed herein, when connected to the sensor disclosed herein is able to adjust the temperature of the liquid to be (Continued)

suitable for the assay, apply a series of potentials, measure the current at several times, measure the diffusion coefficient of the limiting electrochemical species, calculate the concentration of one or more analytes, and rapidly provide the user with the required information on the liquid sample.

17 Claims, 7 Drawing Sheets (51) Int. Cl.
- *G01N 27/327* (2006.01)
- *G01N 33/00* (2006.01)
- *G01N 33/14* (2006.01)

(52) U.S. Cl.
CPC ..... *G01N 33/0042* (2013.01); *G01N 33/0047* (2013.01); *G01N 33/14* (2013.01)

(56) References Cited

U.S. PATENT DOCUMENTS

| | | | |
|---|---|---|---|
| 6,582,573 | B2 | 6/2003 | Douglas et al. |
| 6,638,415 | B1* | 10/2003 | Hodges .................. G01N 33/84 |
| | | | 204/403.02 |
| 6,946,067 | B2* | 9/2005 | Hodges .............. G01N 27/3273 |
| | | | 205/792 |
| 2004/0050717 | A1* | 3/2004 | Teodorczyk ........... C12Q 1/005 |
| | | | 204/403.01 |
| 2005/0160151 | A1* | 7/2005 | Rawson, III .......... G06F 1/3275 |
| | | | 709/213 |
| 2009/0145775 | A1 | 6/2009 | Chu et al. |
| 2010/0062469 | A1 | 3/2010 | Umegae et al. |
| 2011/0213229 | A1 | 9/2011 | Benoit |
| 2013/0075276 | A1* | 3/2013 | Hoashi ................... C12Q 1/004 |
| | | | 204/403.14 |
| 2016/0187283 | A1 | 6/2016 | Cooper et al. |
| 2019/0376930 | A1 | 12/2019 | Arbault et al. |

FOREIGN PATENT DOCUMENTS

| | | |
|---|---|---|
| EP | 1394535 A | 3/2004 |
| EP | 1285266 B1 | 9/2004 |
| EP | 1394535 B1 | 8/2008 |
| EP | 3349009 A1 | 7/2018 |
| WO | 2002008763 A1 | 1/2002 |
| WO | 2002008763 A2 | 1/2002 |
| WO | 2009009656 A1 | 1/2009 |
| WO | 2016030346 A2 | 3/2016 |

* cited by examiner

ELECTROCHEMICAL SENSOR FOR ANALYSIS OF BEVERAGES

CROSS-REFERENCE TO RELATED APPLICATIONS

The present application is a U.S. National Stage entry under 35 U.S.C. § 371 of International Application No. PCT/IB2020/000827 filed on Sep. 30, 2020, designating the United States of America and published in English on Apr. 8, 2021, which claims priority to U.S. Provisional Application Ser. No. 62/908,561 filed on Sep. 30, 2019, each of which is hereby incorporated by reference in its entirety.

BACKGROUND

Field

The invention disclosed herein generally relates to a dry sensor for measuring the concentration of an analyte in a liquid beverage sample which is able to receive a liquid sample and adjust the pH of the liquid to be suitable for assaying an analyte of interest.

Background

It is important to detect the concentration of analytes at various time points during the manufacture and storage of beverages. The composition of beverages must be carefully monitored and controlled throughout manufacturing and storage so that the final product is tasty, attractive and free of microbial contamination. To achieve this, the concentrations of preservatives, flavour compounds, etc. are monitored and controlled at every stage of the process.

Sulphur dioxide (SO2) is an important preservative in the wine industry, the concentration of which must be tightly controlled. If the concentration of SO2 is too low, microbial growth can spoil the wine. However, if the concentration of SO2 is too high, the flavour of the wine is compromised.

The most reliable method of measuring SO2 to date (the aeration-oxidation method) requires acidification of the wine with phosphoric acid (to convert dissolved sulphite ions into SO2 gas), bubbling air through the acidified solution (thus leaving behind potential interferents), transfer of the SO2 gas into a separate solution containing hydrogen peroxide (to oxidize the SO2 to sulphuric acid), and finally titration of the sulphuric acid with a known concentration of sodium hydroxide. These steps can be performed manually by a trained operator over a 15-minute period, or they can be performed automatically using laboratory instruments which cost up to AUD 200,000.

Malic acid, glucose and fructose are important flavour compounds in wine. Standard methods of measuring these substances include mixing the wine with a pH buffer, adding one or more enzymes and a chromogenic compound, and measuring changes in light absorption in a spectrophotometer.

These standard procedures require transport of the wine to a laboratory, the use of expensive and specialised equipment that requires maintenance and calibration by trained laboratory personnel, and a lengthy manual procedure. The overall result is accurate but expensive and inconvenient, and it can take several hours before the vintner is informed of the results.

Less expensive dipstick methods are available for measuring sulphite, but they are inaccurate because an operator has to manually read the intensity of the colour (e.g., shades of pink).

Laboratory electrochemical methods have been developed to measure sulphite (e.g., Caldwell et al. (1991) *Analyst* 116:253-256) but they require polishing of a glassy carbon electrode between each measurement. This time-consuming, manual step can add several minutes to each assay. Moreover, the polishing method requires expertise and is not suitable for a thin-film electrode.

The invention described herein allows several critical parameters in wine to be measured accurately and rapidly using single use strip sensors. There is no requirement for transport of the wine to a specialised laboratory staffed by trained personnel, and no requirement for calibration and maintenance of the equipment. In addition, no liquid waste is generated during the operation of the sensor.

SUMMARY OF INVENTION

The invention disclosed herein relates to methods and sensors for analysing a beverage sample, in particular, a fermented beverage, such as a wine, spirit, kombucha, kefir or beer, or milk, buttermilk, or fruit juice, and the like, in order to detect the presence of an analyte of interest. Analytes of interest can include, for example, but not limited to, free sulphur dioxide, total sugar, glucose, fructose, malic acid, and the like.

The invention is described with particular reference to a sensor for measuring the concentration of free sulphur dioxide, total sugar, glucose, fructose, and malic acid, but it will be understood not to be limited to that particular use and is applicable to other analytic determinations.

Embodiments of the invention described herein relate to a dry sensor for analysing a liquid beverage sample such as wine, spirit, kombucha, kefir, beer, milk, buttermilk, or fruit juice and the like. In some embodiments, the device and methods disclosed herein include a single use strip sensor (hereinafter "sensor") and a meter. In some embodiments, the sensor is a dry sensor which is capable of adjusting the pH of the liquid sample to be suitable for assaying an analyte.

In some embodiments, the invention further includes a meter, wherein the meter is capable of adjusting the temperature of the liquid sample to be suitable for the assay. In some embodiments, the meter is capable of applying a series of potentials, measuring current versus time, subtracting the background signal, determining the diffusion coefficient of the limiting electrochemical species, calculating the concentration of one or more analytes, and providing the user with the required information on the liquid sample without generating liquid waste.

In some embodiments, the invention disclosed herein is a system comprising the sensor and the meter, wherein the system operates at a range of ambient temperatures, solution pH values, and solution viscosities.

In some embodiments, the invention disclosed herein is a sensor for assessing an analyte of interest in a liquid beverage sample, wherein the sensor includes a first electrode, a second electrode, and an opposing surface. In some embodiments, the opposing surface can comprise the second electrode. Thus, some embodiments are directed to an opposing-electrode sensor, i.e., a first electrode and a second electrode facing each other. In some embodiments, the opposing surface is a plain opposing surface. For example, in some embodiments the electrodes are co-planar.

In embodiments of the invention described herein, the first electrode is coated with a reagent which includes an electroactive species and the opposing surface is coated with a pH modifying reagent capable of adjusting the pH of the liquid sample to be suitable for assaying the analyte of interest, wherein the sensor detects a redox reaction in the presence of the liquid beverage sample.

In some embodiments, the opposing surface is coated with a reagent to alter the pH of the liquid sample described herein as "a pH modifying reagent." In some embodiments, the desired pH is between 1 and 3, as in the case of SO2. In some embodiments, the desired pH is between 4 and 5, 6 and 9 or other pH range that is suitable for conducting the desired chemical reagents when the sensor is performing an assay.

In some embodiments, the pH modifying reagent is acidic, such as oxalic acid or other acids that are solid over the specified operating and storage temperature range of the sensor. Examples of suitable acids include oxalic acid, citraconic acid, mellitic acid, camphorsulphonic acid and other acids with a suitable pH and stability over the operating and storage conditions of the sensor. In some embodiments, the pH modifying reagent is a mixture of two or more acids. In some embodiments, the pH modifying reagent is a mixture of oxalic acid and citraconic acid.

In some embodiments, the pH modifying reagent is basic, such as, sodium hydroxide or other bases that are solid over the specified operating and storage temperature range of the sensor. Examples of suitable bases include, sodium hydroxide, potassium hydroxide, tripotassium phosphate, Tris(hydroxymethyl)aminomethane, N-[Tris(Hydroxy Methyl)Methyl]-3-Aminopropanesulfonic Acid, N-cyclohexyl-3-aminopropanesulfonic acid, 4-(2-hydroxyethyl)-1-piperazineethanesulfonic acid, pyrophosphate salts and other bases with a suitable pH and stability over the operating and storage conditions of the sensor. In some embodiments, the base is a mixture of N-[Tris(Hydroxy Methyl)Methyl]-3-Aminopropanesulfonic Acid and sodium hydroxide. In some embodiments a concentrated buffer is used. In some embodiments the pH modifying reagent comprises a suitable buffer and a suitable base, or a combination or mixture thereof.

In some embodiments, the first electrode is coated with a dried-down reagent which includes an electroactive species. In some embodiments, the electroactive species is nicotinamide adenine dinucleotide, potassium ferricyanide, potassium ferrocyanide, ferric ethylenediaminetetraacetic acid, phenazine ethosulfate, 1,2-napthoquinone-4-sulfonic acid or a combination or mixture thereof. In some embodiments, the electroactive species is potassium ferrocyanide. In some embodiments, the electroactive species is potassium ferricyanide.

In some embodiments, the analyte of interest is glucose, fructose and malic acid and the electroactive species is ferricyanide or ferric ethylenediaminetetraacetic acid. In some embodiments, the analyte of interest is SO2 and the electroactive species is ferrocyanide.

In some embodiments, the sensor further includes an enzyme, such as, for example, but not limited to, malate dehydrogenase, glutamic oxaloacetic transaminase, aspartate transaminase, diaphorase, or a combination or mixture thereof. In some embodiments, the sensor further includes fructose dehydrogenase.

In some embodiments, the sensor further includes a glucose selective enzyme, for example, a glucose dehydrogenase enzyme or a glucose oxidase enzyme. In some embodiments, the first electrode is coated with potassium ferricyanide and the sensor further includes a glucose selective enzyme, for example GDH-PQQ, FAD-GDH or GOD (GDH stands for glucose dehydrogenase; PQQ stands for pyrrolo-quinoline-quinone; FAD stands for flavin adenine dinucleotide and GOD stands for glucose oxidoreductase).

In exemplary embodiments, the analyte of interest is SO2. In some embodiments, the pH modifying reagent is a mixture of N-[Tris(Hydroxy Methyl)Methyl]-3-Aminopropanesulfonic Acid and sodium hydroxide and the electroactive species is potassium ferrocyanide. In some embodiments, the SO2 reacts directly with the electrode.

In exemplary embodiments, the analyte of interest is glucose. In some embodiments, the electroactive species is potassium ferricyanide. In some embodiments, the reagent further includes a glucose selective enzyme. In some embodiments, the reagent further includes FAD-GAH. In some embodiments, the reagent further includes GOD. In some embodiments, the pH modifying reagent comprises N-[Tris(Hydroxy Methyl)Methyl]-3-Aminopropanesulfonic Acid.

In exemplary embodiments, the analyte of interest is fructose. In some embodiments, the electroactive species is potassium ferricyanide and the pH modifying reagent comprises N-[Tris(Hydroxy Methyl)Methyl]-3-Aminopropanesulfonic Acid.

In exemplary embodiments, the analyte of interest is malic acid. In some embodiments the electroactive species is ferric ethylenediaminetetraacetic acid, phenazine ethosulfate and/or nicotinamide adenine dinucleotide and the pH modifying reagent is a mixture of N-[Tris(Hydroxy Methyl)Methyl]-3-Aminopropanesulfonic Acid and sodium hydroxide.

In some embodiments, the effects of viscosity are corrected by the systems and/or algorithms that form a part of this invention. Thus, in some embodiments, it is not necessary to control the viscosity within a certain range.

In some embodiments, the temperature of the strip is controlled, such as by heating the strip. In some embodiments, the meter heats the strip by passing current through a resistive element, for example.

In some embodiments, the desired temperature is from about 5° C. to about 45° C. In some embodiments, the desired temperature is from about 10° C. to about 45° C. In some embodiments, the desired temperature is from about 15° C. to about 45° C. In some embodiments, the desired temperature is from about 20° C. to about 45° C. In some embodiments, the desired temperature is from about 25° C. to about 45° C. In some embodiments, the desired temperature is from about 30° C. to about 45°. In some embodiments, the desired temperature is from about 35° C. to about 45°. In some embodiments, the desired temperature is from about 40° C. to about 45° C.

Other embodiments of the invention are directed to methods of using the sensors and strips of the invention disclosed herein.

In the invention disclosed herein, the sensor connects electrically to a meter. In some embodiments, the meter applies predetermined voltages or currents to the strip and measures the resulting current or voltage. As one of skill in the art will appreciate, these methods are known, for example, as amperometry or galvanostatic electrochemical techniques, respectively.

In some embodiments, a pulsing sequence is applied comprising a series of predetermined potentials for predetermined periods of time.

In some embodiments, pulsed voltammetry is employed. In some embodiments, the meter slowly ramps the potential from about 0 to about 1 V and applies square wave or sinusoidal pulses on top of the ramp. In some embodiments, the pulses are applied with an amplitude of about 1 to about 100 mV and a frequency of about 1 to about 1000 Hz. In some embodiments, DC chronopotentiometry is employed, and the meter applies a constant potential of about 50 to about 900 mV lasting for about 0.1 to about 1000 seconds.

In some embodiments, the meter is capable of adjusting the temperature of the liquid sample to be suitable for the assay. In some embodiments, the meter calculates, records, displays and/or transmits the result of the reaction. For example, in some embodiments, current versus time is measured. In some embodiments the meter measures current versus time. In some embodiments the measurements are corrected for background signal and the accuracy of the reading increased (error reduced). In some embodiments, the meter subtracts the background signal. In some embodiments, the diffusion coefficient of the limiting electrochemical species is determined. In some embodiments, the concentration of one or more analytes is calculated. In some embodiments, the meter calculates the concentration of the analyte of interest. In some embodiments, the meter displays the information to the user.

DETAILS OF INVENTION

The invention disclosed herein makes use of electrochemical sensors which can be mass produced using methods analogous to those employed to manufacture the One-Touch® Verio® glucose sensor (marketed by LifeScan) and the Xprecia Stride™ blood coagulation sensor (marketed by Siemens Healthineers).

As used herein, the term "pH modifying reagent" or "pH modifying agent" refers to a reagent that when mixed into an aqueous solution changes the concentration of protons and hydroxide ions present in the solution. For example, a pH modifying reagent is a reagent which is able to either donate protons to the liquid sample (to decrease the pH) or accept protons from the liquid sample (to increase the pH). Exemplary pH modifying reagents include, but are not limited to, acids, such as, oxalic acid, citraconic acid, mellitic acid, camphorsulphonic acid and other acids with a suitable pH and stability over the operating and storage conditions of the sensor, and bases, such as sodium hydroxide, potassium hydroxide, tripotassium phosphate, Tris(hydroxymethyl) aminomethane, N-[Tris(Hydroxy Methyl)Methyl]-3-Aminopropanesulfonic Acid, N-cyclohexyl-3-aminopropanesulfonic acid, 4-(2-hydroxyethyl)-1-piperazineethanesulfonic acid, pyrophosphate salts and other bases with a suitable pH and stability over the operating and storage conditions of the sensor.

As used herein, the term "electroactive species" refers to a species that is capable of either accepting or donating electrons to an electrode. The transfer of electrons may occur between the electroactive species and either an electrode, analyte, enzyme, enzyme cofactor (coenzyme) or secondary mediator. Exemplary electroactive species for use herein include, for example, but are not limited to, nicotinamide adenine dinucleotide, potassium ferricyanide, potassium ferrocyanide, ferric ethylenediaminetetraacetic acid, phenazine ethosulfate, 1,2-napthoquinone-4-sulfonic acid or a combination or mixture thereof. Exemplary embodiments of the invention are discussed in detail below. While specific exemplary embodiments are discussed, it should be understood that this is done for illustration purposes only. A person skilled in the relevant art will recognize that other components and configurations may be used without parting from the spirit and scope of the invention. References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

The invention disclosed herein is directed to a sensor comprising at least two electrodes (e.g., electrodes that can operate as a working electrode, a counter electrode or as both a working electrode and a counter electrode during the assay), none, one or a plurality of enzymes, none, one or a plurality of electrochemical mediators and none, one or a plurality of electroactive species capable of completing the electrochemical circuit by giving up or receiving electrons at a sensor electrode. In some embodiments, one or more reagents are coated on to one or more of the electrodes. As will be described to follow, these sensors can be used by adding a sample to the sensor. The electroactive species can be detected by redox reactions at the electrodes.

The invention described herein can be used in a wide variety of applications, for example, in methods of measuring preservatives and flavouring compounds, such as, free sulphur dioxide, total sugar, glucose, fructose, malic acid, and the like, in a fermented beverage, such as a wine, spirit, kombucha, kefir or beer, or in a beverage such as milk, buttermilk, or fruit juice, and the like.

In embodiments of the invention, the electrodes are composed of a poly(ethylene-terephthalate) (PET) substrate which has been sputtered with a thin layer of an inert electronically conductive material as are known in the art. Other substrate materials can also be used, but PET is particularly preferred as it is very stable under the sensor operating and storage conditions and has a low thermal expansion coefficient. Examples of suitable inert electronically conductive materials are platinum, palladium, iridium, indium oxide, tin oxide, mixtures of indium and tin oxide, carbon and gold. In some embodiments, gold is used as the inert electronically conductive material. In some embodiments, the inert electronically conductive material is coated with a hydrophilic thiol in order to extend the shelf life of the sensor. Examples of hydrophilic coatings are provided in U.S. Pat. No. 6,652,734, entitled "Sensor With Improved Shelf Life," the disclosure of which is incorporated by reference in its entirety.

In some embodiments, the sensor disclosed herein includes opposing electrodes, i.e., the electrodes face one another. In other embodiments, the sensor includes co-planar electrodes. An advantage of opposing electrodes is that the electrode configuration conveniently allows for the determination of the diffusion coefficient of the limiting electrochemical mediator and thus to correct for some of the effects on sensor response of variation in viscosity and/or temperature from assay to assay. This technology is described in International Publication WO 99/09404, entitled "Method and Apparatus for Automatic Analysis," the disclosure of which is incorporated by reference in its entirety.

In the embodiment using co-planar electrodes, it is advantageous for the sensor to further comprise a surface opposing the surface on which the co-planar electrodes are placed. The surface on which the co-planar electrodes are placed is hereinafter referred to as the co-planar electrode surface and the opposing surface is hereinafter referred to as the plain opposing surface. It is advantageous that the plain opposing surface is located such that any reagents that may be coated on the plain opposing surface and dissolve into the test solution can mix through the depth of the solution layer above the co-planar electrode surface by diffusion during the test. This is achieved by locating the plain opposing surface a suitable distance from the co-planar electrode surface. Examples of suitable distance ranges between the co-planar electrode surface and the plain opposing surface are 5 microns to 500 microns, more preferably 20 microns to 200 microns and most preferably 50 microns to 150 microns.

In some embodiments, a first electrode includes a dried-down reagent that includes an electroactive species and one or more additional reagents, such as, an enzyme that reacts selectively with the analyte of interest. For example, in some embodiments, a glucose selective enzyme and potassium ferricyanide can be used to assay glucose (see, e.g., U.S. Pat. No. 9,632,054, entitled "Systems And Methods For High Accuracy Analyte Measurement," the disclosure of which is incorporated herein in its entirety).

In some embodiments, the second electrode, or plain opposing surface, can optionally have a dried-down reagent which is acidic or basic. The acidic or basic reagent can be a strong acid or base (e.g., oxalic acid or sodium hydroxide, respectively) or comprise a compound that has a buffering ability around the desired pH range, as is known in the art. In dry form these reagents are required to be solid over the specified operating and storage temperature range of the sensor. This reagent is designed to alter the pH of the liquid sample so that it falls within the range that is suitable for the reactions that it is desired to be occurring during the assay. For example, many enzymes are most active near neutral pH and less active in the low pH conditions experienced in many beverages, such as wine, spirit, kombucha, kefir, beer, milk, buttermilk, or fruit juice, and the like.

In some embodiments, the two electrodes, or the co-planar electrode surface and the plain opposing surface, are separated by a layer of double-sided tape with adhesive faces (herein after referred to as the double-sided sticky tape), that has at least one section removed from it to define at least one area in the sensor that can allow the passage or containment of the liquid sample or the venting of gases from the sensor as it fills with liquid sample. In some embodiments, the adhesive layer may be comprised of a hot melt adhesive or a pressure sensitive adhesive. The former has advantages since hot melt adhesives are less tacky at ambient temperatures and less likely to transfer to the surfaces of cutting tools during production of the sensors.

In some embodiments, the channel in the double-sided sticky tape overlays the reagents which have been dried onto the electrodes and/or the plain opposing surface. In some embodiments, the walls of the double-sided sticky tape and the surfaces of the electrodes and/or the plain opposing surface define a chamber that will eventually be filled with the liquid to be analysed (e.g., wine, spirit, kombucha, kefir, beer, milk, buttermilk, or fruit juice, and the like).

In some embodiments, the sensor disclosed herein includes opposing electrodes, i.e., the electrodes face one another. In other embodiments, the sensor includes co-planar electrodes. An advantage of opposing electrodes is that the electrode configuration conveniently allows for the determination of the diffusion coefficient of the limiting electrochemical mediator and thus to correct for some of the effects on sensor response of variation in viscosity and/or temperature from assay to assay. This technology is described in International Publication WO 99/09404, entitled "Method and Apparatus for Automatic Analysis," the disclosure of which is incorporated by reference in its entirety.

In some embodiments, a first electrode includes dried-down reagents to react with the particular analyte of interest. For example, in some embodiments, a glucose selective enzyme and potassium ferricyanide can be used to assay glucose (see, e.g., U.S. Pat. No. 9,632,054, entitled "Systems And Methods For High Accuracy Analyte Measurement," the disclosure of which is incorporated herein in its entirety).

In some embodiments, the second electrode can optionally have a dried-down reagent which is acidic or basic. The acidic or basic reagent can be a strong acid or base (e.g., oxalic acid or sodium hydroxide, respectively) or comprise a compound that has a buffering ability around the desired pH range, as is known in the art. In dry form these reagents are required to be solid over the specified operating and storage temperature range of the sensor. This reagent is designed to alter the pH of the liquid sample so that it falls within the range that is suitable for the reactions that it is desired to be occurring during the assay. For example, many enzymes are most active near neutral pH and less active in the low pH conditions experienced in many beverages, such as wine, spirit, kombucha, kefir, beer, milk, buttermilk, or fruit juice, and the like.

The optimal location of various reagents described herein can be determined by various factors including optimizing assay time and instability of particular components at a particular pH. For example, in some embodiments, components of the reagents described herein are dried down with the pH modifying reagent or away from (or opposing to) the pH modifying reagent depending on the instability of each component at high or low pH. In addition, in some embodiments, slow diffusing reactants can be dried down directly on the working electrode and fast diffusing reactants on the counter/reference electrode (or the plain opposing surface) to optimize assay time.

In some embodiments, the two electrodes are separated by a layer of double-sided tape with adhesive faces (herein after referred to as the double-sided sticky tape), that has at least one section removed from it to define at least one area in the sensor that can allow the passage or containment of the liquid sample or the venting of gases from the sensor as it fills with liquid sample. In some embodiments, the adhesive layer may be comprised of a hot melt adhesive or a pressure sensitive adhesive. The former has advantages since hot melt adhesives are less tacky at ambient temperatures and less likely to transfer to the surfaces of cutting tools during production of the sensors.

In some embodiments, the channel in the double-sided sticky tape overlays the reagents which have been dried onto the electrodes. In some embodiments, the walls of the double-sided sticky tape and the surfaces of the electrodes define a chamber that will eventually be filled with the liquid to be analysed (e.g., wine, spirit, kombucha, kefir, beer, milk, buttermilk, or fruit juice, and the like).

In some embodiments, it can be advantageous to control the temperature of the strip. Ambient temperatures can vary widely (e.g., 5-45° C.) and this can affect the electrochemical response. Secondly, certain reactions (e.g., those catalysed by enzymes) can be most efficient over a narrow temperature range: if the temperature is too low, the reaction is too slow but if the temperature is too high, the enzyme will denature and be ineffective. In some embodiments, it is best to heat the strip to a particular temperature rather than trying to cool the strip to a set temperature: this is because heating components are less expensive and can require less energy than cooling components to achieve the desired temperature.

Figure 1:
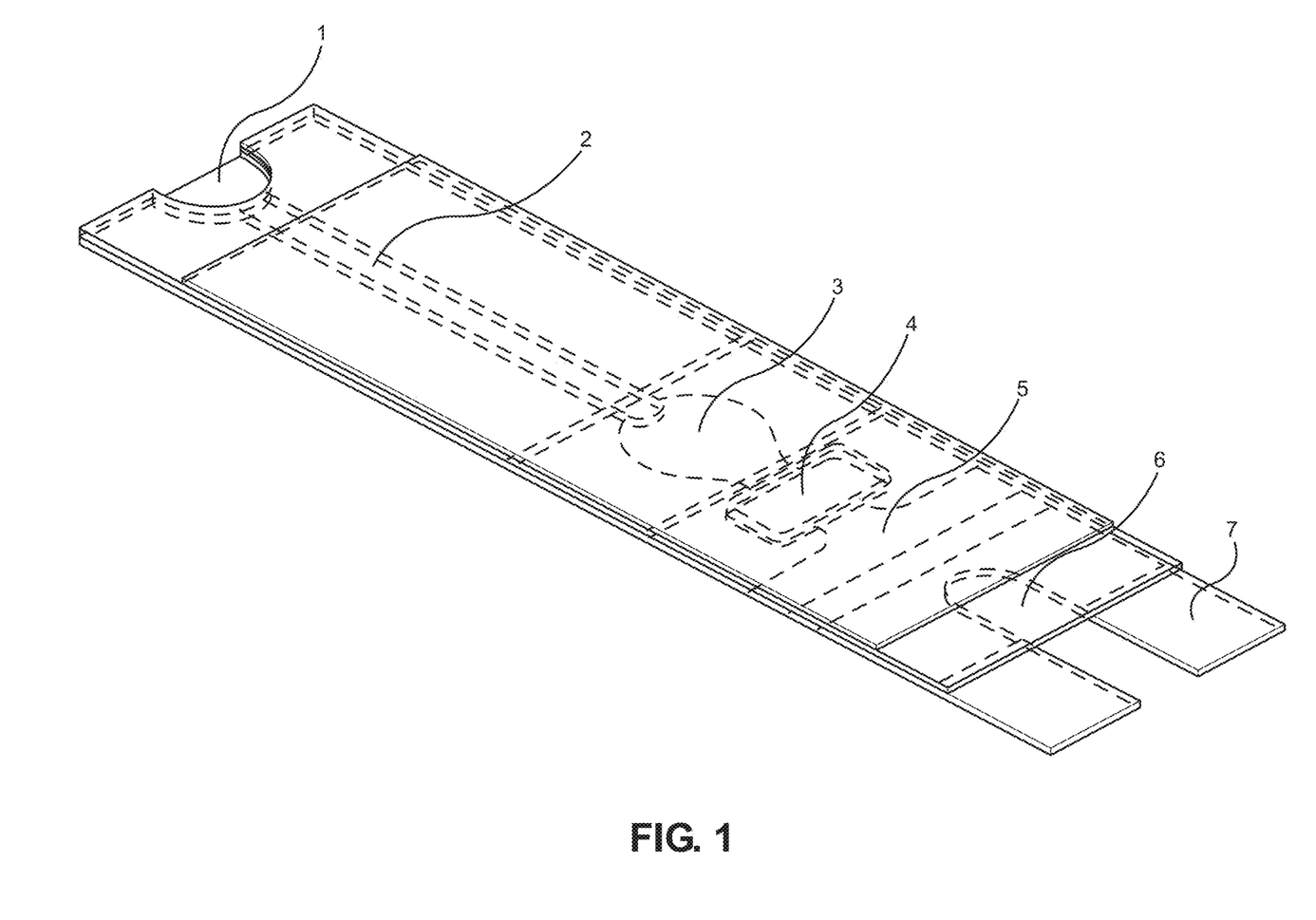
FIG. 1 is a schematic diagram of an exemplary sensor with opposing electrodes.
Figure 2:
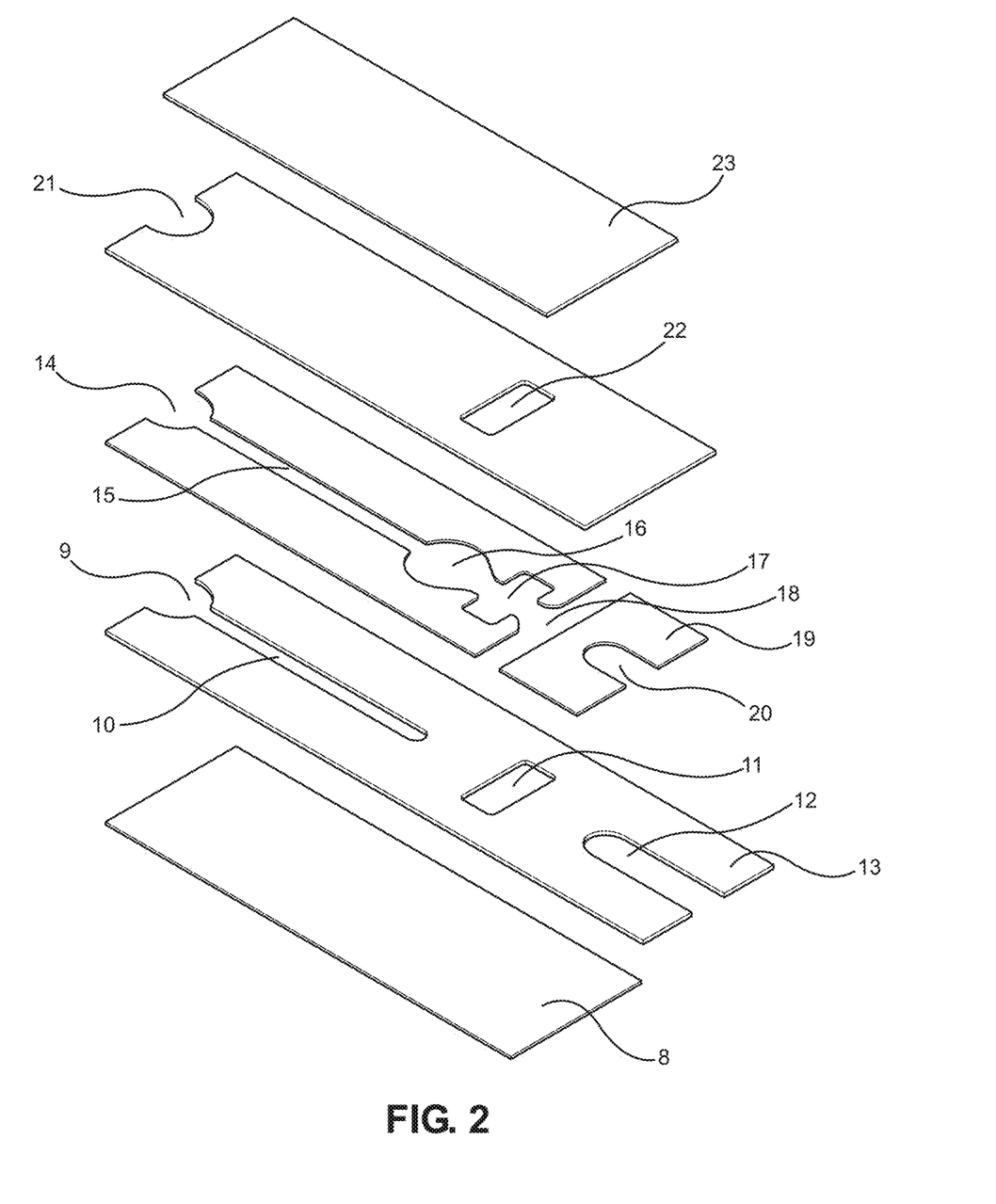
FIG. 2 is a diagram showing an exploded view of the exemplary test strip shown in FIG. 1.

An example of a sensor made with opposed electrodes is shown in FIG. 1 and described in more detail in FIG. 2.

FIG. 1 shows a schematic diagram of the sensor. A droplet of liquid sample (such as wine, spirit, kombucha, kefir, beer, milk, buttermilk, or fruit juice, and the like) is placed on the porch (1). Surface tension considerations cause the liquid to travel up the capillary fill channel (2), enter the reaction/detection chamber (3), and proceed no further due to the "stop hole" (4). This allows a defined volume of liquid to react with the reagent dried in the reaction/detection chamber (3). In rare instances where the liquid gets past the stop hole then the liquid is contained within the "flood plain" (5). This mechanism stops the liquid in the sensor from contaminating the meter. A cutout through some layers of the sensor (6) allows the meter to make contact with the upper electrode. Two prongs (7) allow the meter to make contact with the lower electrode.

The surface energy considerations required to ensure that the liquid moves along the fill channel and enters the reaction/detection chamber are described in U.S. Pat. No. 6,939,312, entitled "Method And Device For Sampling And Analyzing Interstitial Fluid And Whole Blood Samples," the disclosure of which is hereby incorporated by reference in its entirety.

FIG. 2 shows an exploded view of the five layers in the sensor. In some embodiments, the first (lowest) layer (8) is the "hydrophilic floor" made by coating PET with a mixture of a water-soluble hot-melt adhesive (Adhesives Research, JLF-19DEC19-1 or JLF-19DEC19-2Eastman Kodak).

In some embodiments, the second layer is an electrode made of PET sputtered with gold. The electrode has punched out sections to form a "porch" (9), a "fill channel" (10), a "stop hole" (11) and a "gap" (12). The two prongs (13) on either side of the gap allow the meter to connect to the electrode. In some embodiments, the electrode is coated with a hydrophilic thiol layer. In some embodiments, the area of the electrode between the fill channel and the stop hole is further coated with one or more reagents that can react with the analyte of interest.

In some embodiments, the third layer is a double-sided sticky tape with several features cut into it, including those for forming the "porch" (14), "fill channel" (15), the "reaction/detection chamber" (16), the "stop hole" (17), the "flood plain" (18), and a "gap" (20) which allows the electrodes to connect to a potentiostat such as a hand held meter (to be further described below). The two arms of the double-sided sticky tape (19) on either side of the gap keep the two electrodes apart so that they do not touch one another and cause an electrical short.

In some embodiments, the fourth layer is an electrode made of PET sputtered with gold. The electrode has punched out sections to form a "porch" (21) and a "stop hole" (22). In some embodiments, the electrode is coated with a hydrophilic thiol layer, and further coated with pH modifying species such as oxalic acid, sodium hydroxide or tripotassium phosphate. In some embodiments, the pH modifying species is coated on the region that corresponds to the "reaction/detection chamber," or on the region that corresponds to the "fill channel." The advantage of the latter approach will become apparent when the correction for antioxidants is described below.

The fifth (topmost) layer is the "ceiling" (23) and in some embodiments is made of PET coated with an adhesive. In some embodiments, this layer may optionally include a barcode tape which can contain information such as the identity of the analyte, the manufacturing batch number, expiry date, calibration parameters, and the like.

When all five layers are laminated together, they form the completed sensor shown in FIG. 1. In some embodiments, the two "prongs" on the left-hand side of the sensor are inserted into a meter (potentiostat). In some embodiments, the meter heats the sensor to the required temperature. The liquid to be analysed is placed on the "porch" on the right-hand side of the sensor. The liquid moves along the fill channel (aided by the hydrophilic floor), enters the detection chamber, and does not enter the stop hole. The liquid dissolves the reagents, is adjusted to an appropriate pH, and reacts with the reagents. The meter applies a voltage pulse sequence between the upper and lower electrodes. The resulting current versus time transient is then analysed with an algorithm. The analysis includes a measurement of the diffusion coefficient of the limiting electrochemical species, measurement of the background current, subtraction of the background current from the total current, division of the corrected current by the diffusion coefficient, and conversion of the signal to the final value (such as the concentration of a particular analyte) using calibration parameters.

Particular embodiments of the sensor are described in the following examples.

EXAMPLES

Example 1. Sulphur Dioxide Sensor

"Reaction/detection chambers" and a "flood plain" were kisscut into double-sided sticky tape (with a release liner on each side of the tape) using rotary conversion processes.

A solution of 80 mM potassium ferrocyanide+1 mg/mL Pluronic F87 was pumped at 800 microlitres per minute through an 8-gauge stainless steel blunt pipetting needle. The function of the ferrocyanide is to "complete the circuit" so that when SO2 accepts an electron from the cathode on one side of the strip then ferrocyanide donates an electron to the anode on the other side of the strip.

The stream of ferrocyanide solution was deposited onto an electrode which was moving at a continuous speed of 10 metres per minute. The liquid was dried under infrared bulbs. This formed the lower electrode. The double-sided sticky tape was laminated onto the lower electrode in such a way that the reaction/detection chambers overlapped the dried reagent. The fill channel was punched into the bilaminate using a male punch and female die set. The "gap" (labelled as 12 in FIG. 2) was also punched at the same time.

A solution of 4.5 M citraconic acid+110 mM oxalic acid+1 mg/mL Pluronic F87 was deposited onto the upper electrode and dried as described above. In this instance, the acids were dried on a region which corresponded to the "reaction/detection chamber." However, in some embodiments the acids can be dried on a region which corresponds to the "fill channel." The upper electrode was laminated to the double-sided sticky tape so that the upper electrode faced the lower electrode. The porch and stop hole were punched into the trilaminate at the same time using a male punch and female die set.

The hydrophilic floor was laminated below the lower electrode, and the ceiling layer was laminated above the upper electrode. The quinlaminate was cut into individual strips. This completed the manufacture of the strips.

The final strip configuration was 8 mm wide and 30 mm long. The area of the bottom working electrode was 0.1128 sq. cm, and the electrodes were 95 micrometres apart. It will be apparent to one skilled in the art that other dimensions and geometries also fall within the scope of this invention.

Various wines were tested using the sulfur dioxide strip at the Australian Wine Research Institute. Tests were performed using a meter which heats the sensor to 32 degree Celsius. A droplet of wine (≥6 microlitre) was loaded onto the porch area of the sensor. After detection of the sample, a specified voltage sequence is applied. This voltage sequence consists of a 5 second wait followed by a square wave pulse sequence (40 mV peak to trough, 38.5 Hz) on top of a linear voltage ramp (increasing by 4 mV per cycle). In practice, at the start of each cycle the potential was stepped up 44 mV, held constant for 13 milliseconds, and then stepped down 40 mV and held constant for a further 13 milliseconds. This pulse sequence was based approximately on that used by Caldwell et al (1991) *Analyst* 116:253-256. Square waves were used instead of sinusoidal waves because the former are easier to generate in inexpensive potentiostats. The pulse sequence is followed by a 7 second wait and lastly a 600 mV potential seconds.

The lower electrode was the working electrode since the area of the lower electrode is well-defined by the various cutting and punching processes used to make the sensor.

Currents were measured every 1 millisecond. Each time the potential was stepped up 44 mV, the current rose to a peak value and then decreased to a plateau. Analogously, each time the potential was stepped down 40 mV, the current decreased to a trough value and then increased to a plateau. The parameter of interest was the difference between the higher plateau current and the (previous) lower plateau current. This difference was termed the "delta plateau current" and was plotted versus the potential (see FIG. 5).

Examination of the data obtained from 253 red wines and 218 white wines tested showed that peak height at around 600 mV from the delta plateau currents correlate to the concentration of free sulfur dioxide according to the Thermo Gallery reference analyser. The signal is refined by performing a background subtraction which involves subtracting a fitted an exponential using the delta plateau current at 420 mV and 100 mV beyond the trough of the sulfur dioxide peak.

This approach allows the background signal in each wine to be subtracted from the total signal. The difference yields the signal arising only from sulphite. This approach is advantageous because each wine may have a different concentration of background (interferent) electroactive species such as anthocyanins, polyphenols and tannins.

Figure 3:
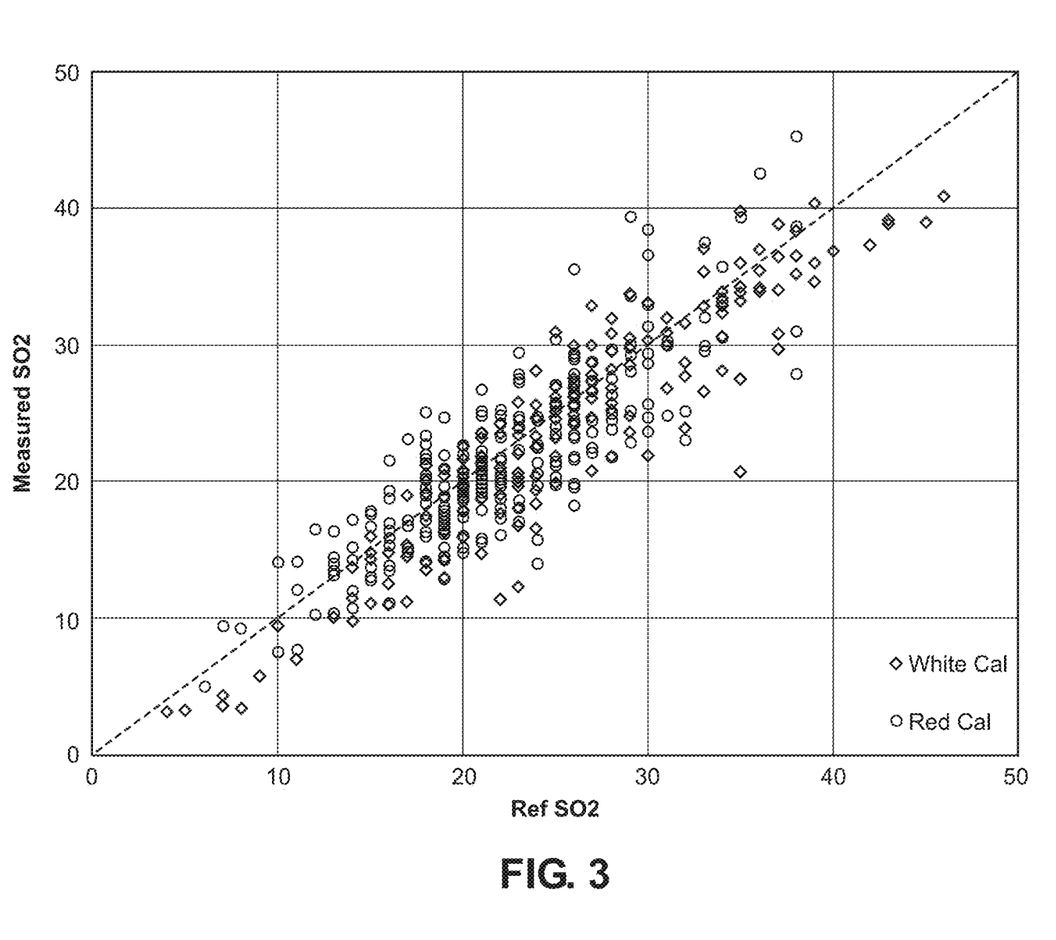
FIG. 3 is a graph showing the measured free sulfur dioxide from the exemplary sensor verses the reference result from the Thermo Gallery reference analyser obtained by the Australian Wine Research Institute, n=471 wines.

The resulting sulfur dioxide signal is calibrated individually for red and white wine. FIG. 3 plots the calibrated measurement against the Thermo Gallery Reference result for all 471 wines tested at the Australian Wine Research Institute.

The short sulfite test described above can be contrasted to the 10-12 minute test published by Caldwell et al. The fast test embodied in this invention also contrasts with the 15-minute aeration-oxidation assay which is the gold standard for sulfite measurement.

The effect of interferences was also assessed. Each wine can have a different concentration of sugar (ranging up to 200 g/L) and this would affect the diffusion coefficient and hence the current.

The error arising from varying concentrations of sugar was reduced by using the measured diffusion coefficient in the algorithm. At the end of the pulse voltammetry sequence, the meter waited for 7 seconds (in order to allow all species to randomise so that there are no concentration gradients) and then applied a continuous 600 mV pulse for 3 seconds. The current versus time transient was analysed essentially according to the method disclosed in International Publication No. WO 99/09404, the disclosure of which is hereby incorporated by reference in its entirety.

1) Identify the maximum current obtained (soon after applying the constant 600 mV pulse) as well as the minimum current (MINi; towards the end of the 600 mV pulse).
2) Select the section of the 600 mV transient which falls between 1.05*MINi and 1.43*MINI. This corresponds to the range of the decay which is well fitted by a single exponential function (plus an offset).
3) Generate a plot of $\ln(i(t)/MINi-1)$ versus time.
4) Calculate the slope of the plot.
5) $D=-slope*0.0095^2/(4\pi^2)$, where 0.0095 is the number of cm between the two electrodes. The units of D are $cm^2s^{-1}$.
6) Multiply D by $10^6$ in order to get more manageable numbers.
7) Divide the previous raw signal (peak current in pulsed voltammetry) by D.
8) This forms the new raw signal for the calibration process.

The improvement in the accuracy of the measured SO2 is shown in Table 1. The error in the measurement of SO2 was close to −30% when 220 g/L sugar was spiked into wine (see the bold numbers in the fourth column of Table 1). However, once the readings were corrected based on the measured diffusion coefficient the worst case error was only 11%.

Example 2. Total Sugar Sensor

Figure 4A:
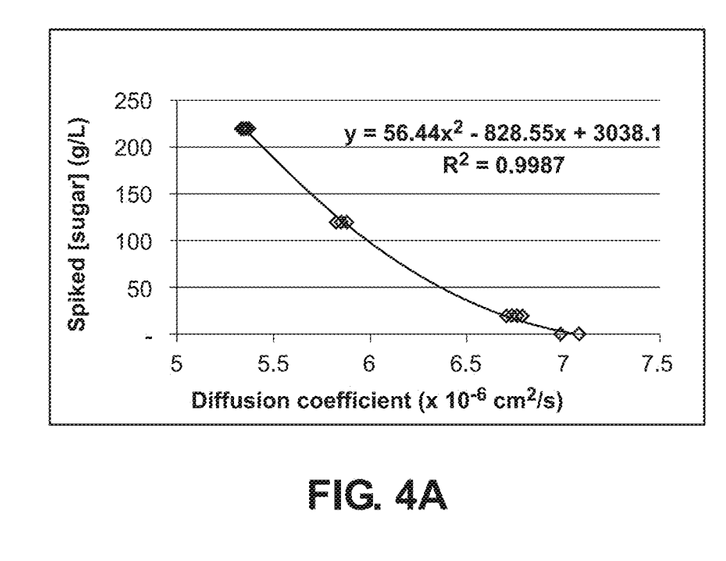
FIG. 4a is a plot showing sugar versus D using the data in Table 1 and fit with a quadratic.

The concentration of sugar versus D was plotted using the data in Table 1, and the points fit with a quadratic (see FIG. 4A).

Figure 4B:
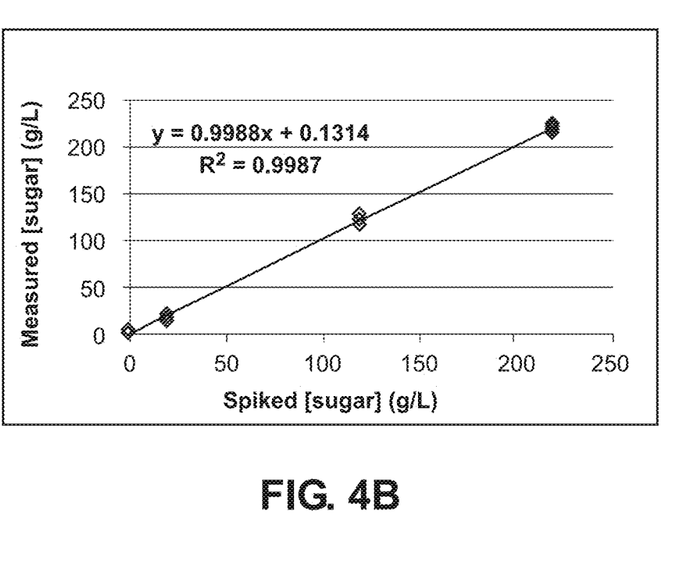
FIG. 4b is a plot showing total concentration of sugar (sucrose+fructose+glucose).

Given the measured value of D and the fit equation, the meter was able to predict the total concentration of sugar (sucrose+fructose+glucose) as shown in FIG. 4B.

Total sugar was analogous to the "Brix value" which is routinely measured by vintners (based on density or refractive index).

Example 3. Glucose Sensor Containing GDH-PQQ

A glucose sensor was constructed using a variation to the method described above for sulphite sensors. The glucose assay chemistry and algorithm can be adapted from U.S. Pat.

No. 7,291,256, entitled "Mediator Stabilized Reagent Compositions And Methods For Their Use In Electrochemical Analyte Detection Assays," or from U.S. Pat. No. 8,404,102, entitled "Method And Apparatus For Rapid Electrochemical Analysis," or from U.S. Pat. No. 8,916,040, entitled "System And Method For Measuring An Analyte In A Sample," or from U.S. Pat. No. 9,632,054, entitled "Systems And Methods For High Accuracy Analyte Measurement," the disclosure of each of which is incorporated by reference in its entirety.

The lower electrode was striped with 900 mM potassium ferricyanide and 20 mg/mL FAD-GDH (GDH stands for glucose dehydrogenase; FAD stands for flavin adenine dinucleotide). The upper electrode was striped with 200 mM sodium hydroxide in order to adjust the pH of wine to a range which is more suitable for GDH.

The following voltage pulse sequence was used. +20 mV applied for one (1) second (where the upper electrode is the anode), +300 mV applied for three (3) seconds, and finally −300 mV applied for one (1) second. Currents were measured every ten (10) milliseconds and averaged over a fifty (50) millisecond period.

Figure 5:
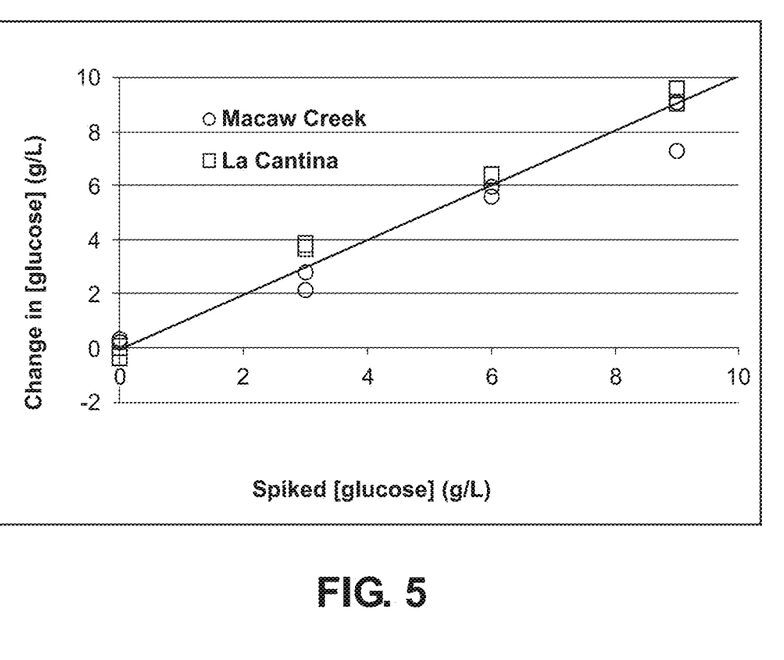
FIG. 5 is a plot showing concentrations of glucose for two (2) wines spiked with various concentrations of glucose.

Two wines were spiked with various concentrations of glucose and tested in the strips. The results are shown in FIG. 5.

In this example, the sodium hydroxide was dried on a region which corresponded to the "reaction/detection chamber." However, in some embodiments the sodium hydroxide can be dried on a region which corresponds to the "fill channel." The advantage of the latter approach is that it is possible to correct for antioxidants using the invention described in U.S. Pat. No. 8,163,162, entitled "Methods And Apparatus For Analyzing A Sample In The Presence Of Interferents," the disclosure of which is incorporated by reference in its entirety.

Example 4. Glucose Sensor Containing GOD

A glucose sensor was constructed using a variation to the method described above for sulphite sensors. The glucose assay chemistry and algorithm can be adapted from U.S. Pat. No. 7,291,256, entitled "Mediator Stabilized Reagent Compositions And Methods For Their Use In Electrochemical Analyte Detection Assays," or from U.S. Pat. No. 8,404,102, entitled "Method And Apparatus For Rapid Electrochemical Analysis," or from U.S. Pat. No. 8,916,040, entitled "System And Method For Measuring An Analyte In A Sample," or from U.S. Pat. No. 9,632,054, entitled "Systems And Methods For High Accuracy Analyte Measurement," the disclosure of each of which is incorporated by reference in its entirety.

The lower electrode was striped with reagents comprising 0.498 g/L Pluronic P103 (BASF), 0.258 g/L Pluronic F87 (BASF), 0.300 g/L citraconic acid, 10.00 g/L dipotassium citraconate, 15.36 g/L sucrose dissolved in water to form a reagent buffer. To this was added 29.63 g/100 g of reagent buffer potassium ferricyanide and 112 mg/100 g of reagent buffer of glucose oxidoreductase from *Aspergillus Niger* (GOD). The upper electrode was striped with 100 mM Tris(hydroxymethyl)aminomethane base in order to adjust the pH of wine to a range that is more suitable for the oxidation of glucose catalysed by GOD.

The following voltage pulse sequence was used. +20 mV applied for one (1) second (where the upper electrode is the anode), +300 mV applied for three (3) seconds, and finally −300 mV applied for ten (10) seconds. Currents were measured every ten (10) milliseconds. The current was converted to a glucose concentration using the following algorithm:

$$[\text{glucose}] = ((-i(5)/100)/\wedge r - a \cdot ipp\text{min}/100) - \text{intercept})/\text{slope}$$

where [glucose] is the measured glucose concentration, i(5) is the current flowing at 5 seconds after −300 mV is applied to the sensor, ippmin is the minimum current recorded during the period +300 mV is applied to the sensor and r, a, intercept and slope are adjustable parameters chosen to optimise agreement between [glucose] and the known glucose concentration, measured by a reference instrument during a calibration experiment ([reference glucose]). intercept and slope are the y-axis intercept and the slope respectively determined by applying linear least squares regression to ([reference glucose], [glucose]) data pairs. In this algorithm the term containing i(5) gives a measure of the glucose in the sample plus a sample specific non-glucose related sensor signal. The term containing ippmin is a measure of the sample specific non-glucose related sensor signal only. Subtraction of the two terms is performed as a method for correcting for the non-glucose part of the sensor signal.

Figure 6:
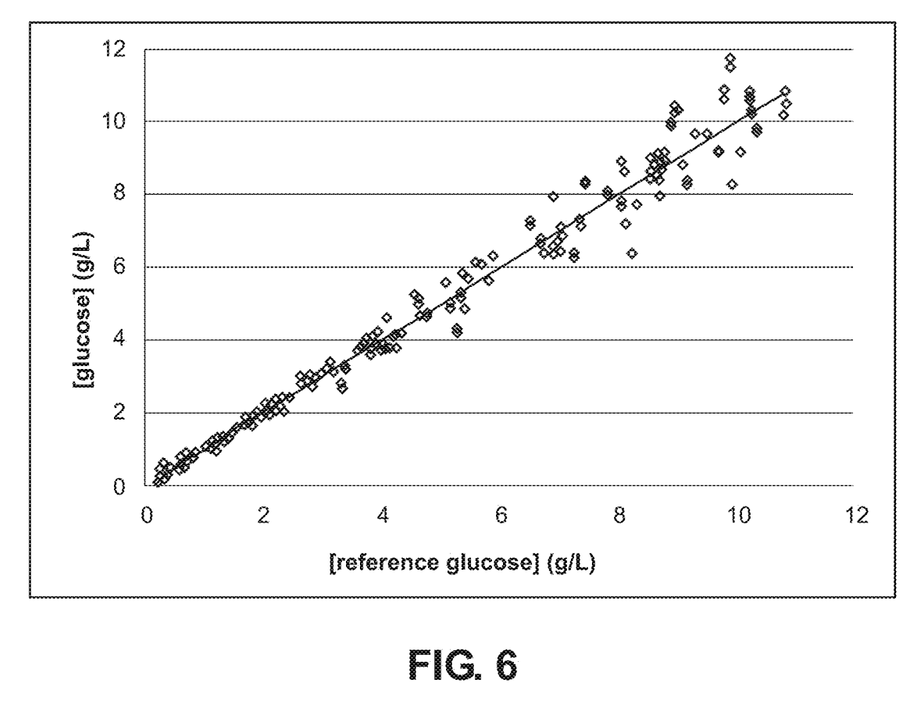
FIG. 6 is a plot showing 12 red wine and 12 white wines spiked with various concentrations of glucose and tested in the strips.

12 red wine and 12 white wines were spiked with various concentrations of glucose and tested in the strips. The results are shown in FIG. 6.

Example 5. Fructose Sensor

It is possible to adapt the chemistry described by Adachi et. al. (*Bioelectrochemistry* (2019) 12:1-9), the disclosure of which is incorporated by reference in its entirety, to make a fructose sensor. D-fructose dehydrogenase from *Gluconobacter* sp. (Sigma) can accept electrons from fructose and pass them on to potassium ferricyanide, thus providing a convenient electrochemistry assay for fructose.

A white wine was spiked with various concentrations of fructose and tested in strips striped with 750 mM ferri on the lower electrode. 10 uL of various [fructose] spiked wine +2 uL 300 mM TRIS base +2 uL 1000 U/mL FDH was tested in strips at 32° C.

Figure 7:
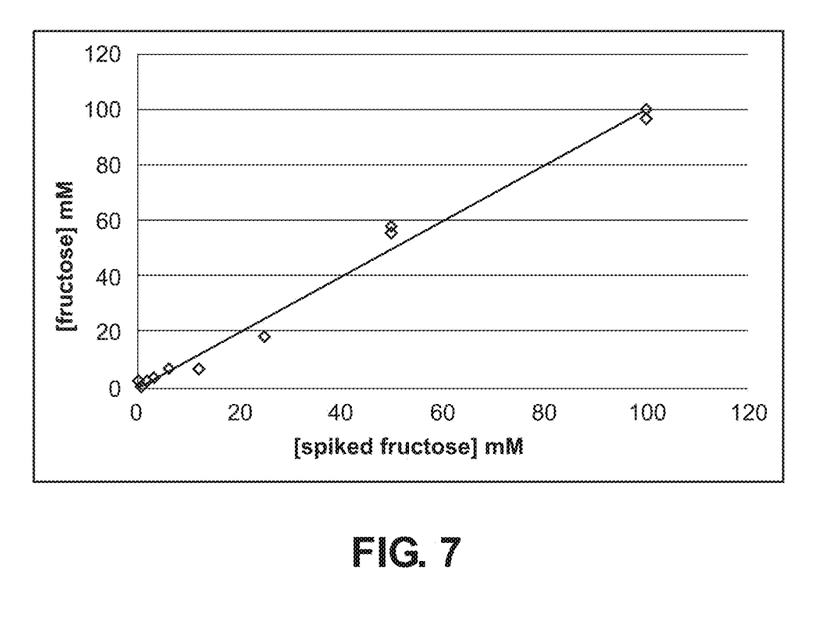
FIG. 7 is a plot showing a white wine spiked with various concentrations of fructose and tested in strips.

The following voltage pulse sequence was used. +20 mV applied for one (1) second (where the upper electrode is the anode), +300 mV applied for three (3) seconds, and finally −300 mV applied for one hundred (100) seconds. Currents were measured every ten (10) milliseconds. The current was converted to a fructose concentration using the following algorithm:

$$[\text{fructose}] = ((-i(20)/\wedge a) - \text{intercept})/\text{slope}$$

where [fructose] is the measured glucose concentration, i(20) is the current flowing at 20 seconds after −300 mV is applied to the sensor, ippmin is the minimum current recorded during the period +300 mV is applied to the sensor and a, intercept and slope are adjustable parameters chosen to optimise agreement between [fructose] and the spiked fructose concentration ([spiked fructose]). The results are shown in FIG. 7.

Example 6. Malic Acid Sensor

The malate dehydrogenase enzyme catalyses the following reaction:

Malate+$NAD^+$→Oxaloacetate+NADH

It is difficult to pick up NADH directly at the electrode, secondary mediators such as ferricyanides or diaphorase are used to channel the electrons from NADH to a secondary mediator such as FeEDTA, or directly to the anode.

The addition of glutamic oxaloacetate transaminase (GOT, aka. aspartate transaminase, AST) and glutamate can promote the formation of NADH by catalysing the transamination of oxaloacetate to aspartate.

A malic acid sensor was constructed using a variation to the methods described in the above sensors.

The lower electrode was striped with reagents comprising 200 mM FeEDTA, 200 mM nicotinamide adenine dinucleotide and 1.00 g/L Pluronic F87 (BASF) dissolved in water. The upper electrode was striped with reagents comprising 1.00 g/L Pluronic F87 (BASF), 2000 U/mL malate dehydrogenase (Toyobo, MAD-211), 200 U/mL diaphorase (Sigma, D5540), 50 mM [tris(hydroxymethyl)methylamino] propanesulfonic acid, 37.5 mM sodium hydroxide and 50 mM sucrose dissolved in water to form a reagent buffer.

The following voltage pulse sequence was used. 0 mV applied for one (1) second, +300 mV applied for three (3) seconds (where the upper electrode is the anode), −300 mV applied for one hundred eighty (180) seconds, 0 mV for ten (10) seconds and finally −300 mV for seven (7) seconds. Currents were measured every fifty (50) milliseconds. The current was converted to a malic acid concentration using the following algorithm.

[malic acid]=(−$i(60)$/\$a$−intercept)/slope where [malic acid] is the measured malic acid concentration, $i(60)$ is the current flowing at 60 seconds after the initial 0 mV is applied to the sensor and a, intercept and slope are adjustable parameters chosen to optimise agreement between [malic acid] and the known malic acid concentration, measured by a reference instrument during a calibration experiment ([reference malic acid]). In this algorithm the term containing $i(60)$ gives a measure of the malic acid in the sample plus a sample specific non-malic acid related sensor signal.

Figure 8:
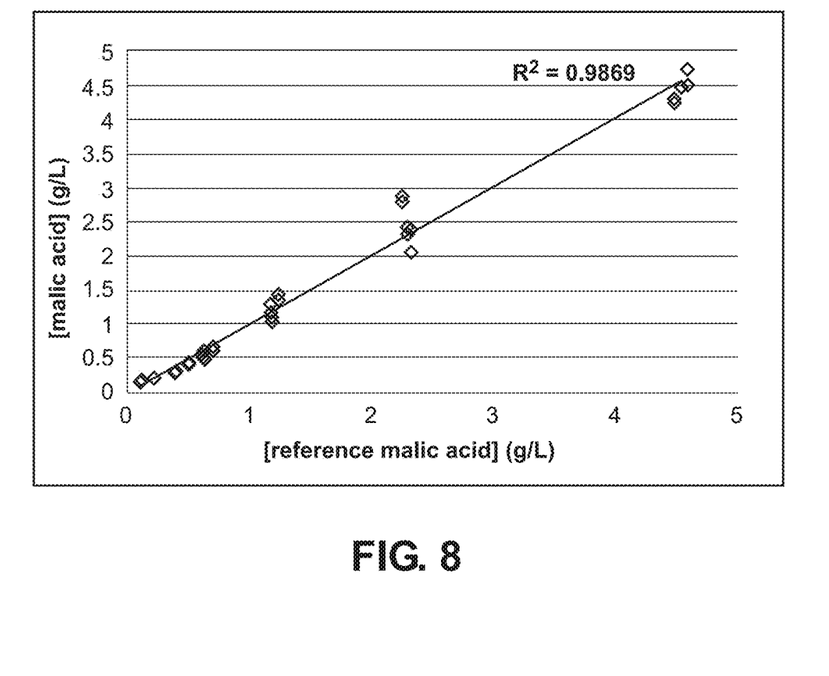
FIG. 8 is a plot showing 3 red wines spiked with various concentrations of malic acid and tested in strips.

3 red wines spiked with various concentrations of malic acid were diluted 10× using 1 M TAPS buffer +750 mM NaOH and tested in the strips. The results are shown in FIG. 8.

It will be apparent to those skilled in the art that the invention can be used to assay many other electrolytes in beverages.

While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents. Any headings used herein are provided solely for organizational purposes and are not intended to impart any division or meaning to this document, unless specifically indicated.

What is claimed is:

1. A sensor for assessing an analyte of interest in a liquid beverage sample, wherein the sensor comprises a first electrode, an opposing surface to the first electrode, and a second electrode, wherein the opposing surface can comprise the second electrode or be a plain opposing surface, wherein the first electrode is coated with a reagent which includes an electroactive species and the opposing surface is coated with a pH modifying reagent capable of adjusting the pH of the liquid sample to be suitable for assaying the analyte of interest, wherein the pH modifying reagent comprises a mixture of citraconic acid and oxalic acid, wherein the sensor is configured to detect a redox reaction in the presence of the liquid beverage sample.

2. The sensor of claim 1, wherein the analyte of interest is free sulphur dioxide, total sugar, glucose, fructose, or malic acid.

3. The sensor of claim 1, wherein the liquid beverage sample is a wine, spirit, kombucha, kefir, beer, milk, buttermilk, or fruit juice.

4. The sensor of claim 1, wherein the pH modifying reagent alters the pH of the liquid sample to between 1 and 3, or between 4 and 5, or between 6 and 9.

5. The sensor of claim 1, wherein the pH modifying reagent comprises a base that is solid over a specified operating and storage temperature range of the sensor.

6. The sensor of claim 5, wherein the base is selected from the group consisting of sodium hydroxide, potassium hydroxide, tripotassium phosphate, Tris(hydroxymethyl) aminomethane, N-[Tris(Hydroxy Methyl)Methyl]-3-Aminopropanesulfonic Acid, N-cyclohexyl-3-aminopropanesulfonic acid, 4-(2-hydroxyethyl)-1-piperazineethanesulfonic acid, and pyrophosphate salts.

7. The sensor of claim 6, wherein the base is sodium hydroxide.

8. The sensor of claim 6, wherein the base is a mixture of N-[Tris(Hydroxy Methyl)Methyl]-3-Aminopropanesulfonic Acid and sodium hydroxide.

9. The sensor of claim 1, wherein the electroactive species comprises nicotinamide adenine dinucleotide, potassium ferricyanide, ferric ethylenediaminetetraacetic acid, phenazine ethosulfate, 1,2-napthoquinone-4-sulfonic acid or a combination or mixture thereof.

10. The sensor of claim 9, wherein the electroactive species comprises potassium ferrocyanide.

11. The sensor of claim 10, wherein the analyte of interest reacts directly with the electrode, and the electroactive species comprises potassium ferrocyanide.

12. The sensor of claim 1, wherein the first electrode or opposing surface is further coated with a glucose selective enzyme.

13. The sensor of claim 12, wherein the glucose selective enzyme is a glucose dehydrogenase enzyme or a glucose oxidase enzyme.

14. The sensor of claim 13, wherein the first electrode is coated with potassium ferricyanide and a glucose selective enzyme.

15. The sensor of claim 13, wherein the first electrode or opposing surface is coated with glucose dehydrogenase-pyrrolo-quinoline-quinone (GDH-PQQ), flavin adenine dinucleotide-glucose dehydrogenase (FAD-GDH) or glucose oxidoreductase (GOD).

16. The sensor of claim 15, wherein the first electrode or opposing surface is coated with FAD-GDH.

17. The sensor of claim 1, wherein the first electrode and second electrode face each other.

* * * * *